(12) United States Patent
Heine et al.

(10) Patent No.: US 7,387,384 B2
(45) Date of Patent: Jun. 17, 2008

(54) OPHTHALMOSCOPE

(75) Inventors: Helmut Heine, Diessen (DE); Oliver Heine, Herrsching (DE); Wolfgang Behrendt, Seefeld (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 44 days.

(21) Appl. No.: 11/354,975

(22) Filed: Feb. 16, 2006

(65) Prior Publication Data
US 2006/0244912 A1    Nov. 2, 2006

(30) Foreign Application Priority Data
May 2, 2005   (DE)   .................. 20 2005 007 013 U

(51) Int. Cl.
*A61B 3/10*   (2006.01)
(52) U.S. Cl. ........................ 351/205; 351/214; 351/221
(58) Field of Classification Search ................ 351/214, 351/221, 205–206, 243–244, 246; 359/368
See application file for complete search history.

(56) References Cited

U.S. PATENT DOCUMENTS 4,684,227 A    8/1987   Schmidt et al.
6,474,815 B1 *  11/2002  Ulbers et al. ............... 351/214

FOREIGN PATENT DOCUMENTS

DE        37 19 123 C1     2/1989
DE       195 31 529 A1     2/1997

* cited by examiner

*Primary Examiner*—Ricky L Mack
*Assistant Examiner*—James R Greece
(74) *Attorney, Agent, or Firm*—Rothwell, Figg, Ernst & Manbeck P.C.

(57) ABSTRACT

An ophthalmoscope includes a housing (12) in which there are arranged an observing unit and a light source between which there are/is arranged a diaphragm and/or a filter device that can be set via a swivel lever device (16, 17) mounted outside on the housing (12). The swivel lever device (16, 17) can be locked in respective latch stages by a locking device (41).

3 Claims, 6 Drawing Sheets

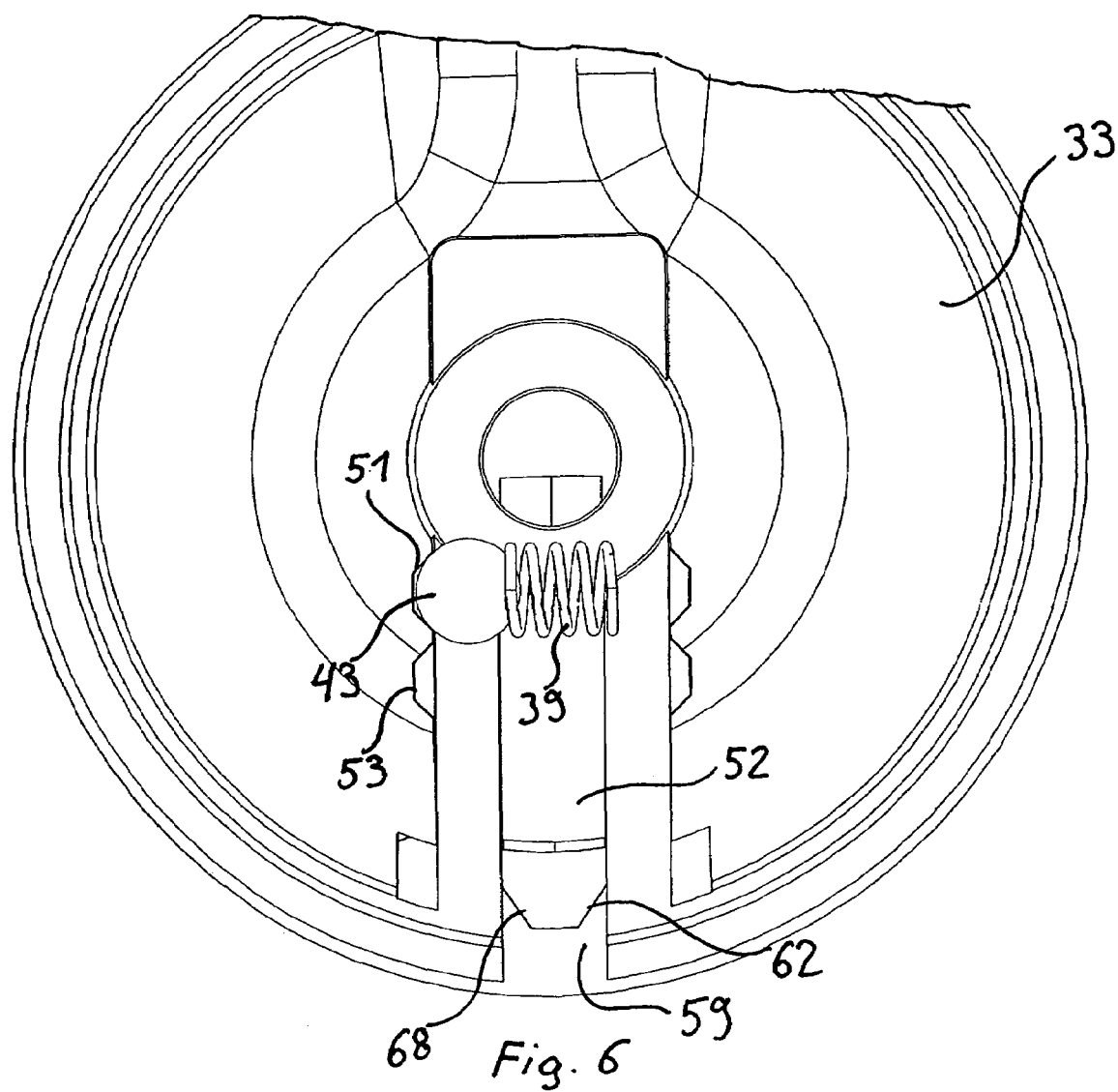

OPHTHALMOSCOPE

BACKGROUND OF THE INVENTION

1. Field of the Invention

Figure 1:
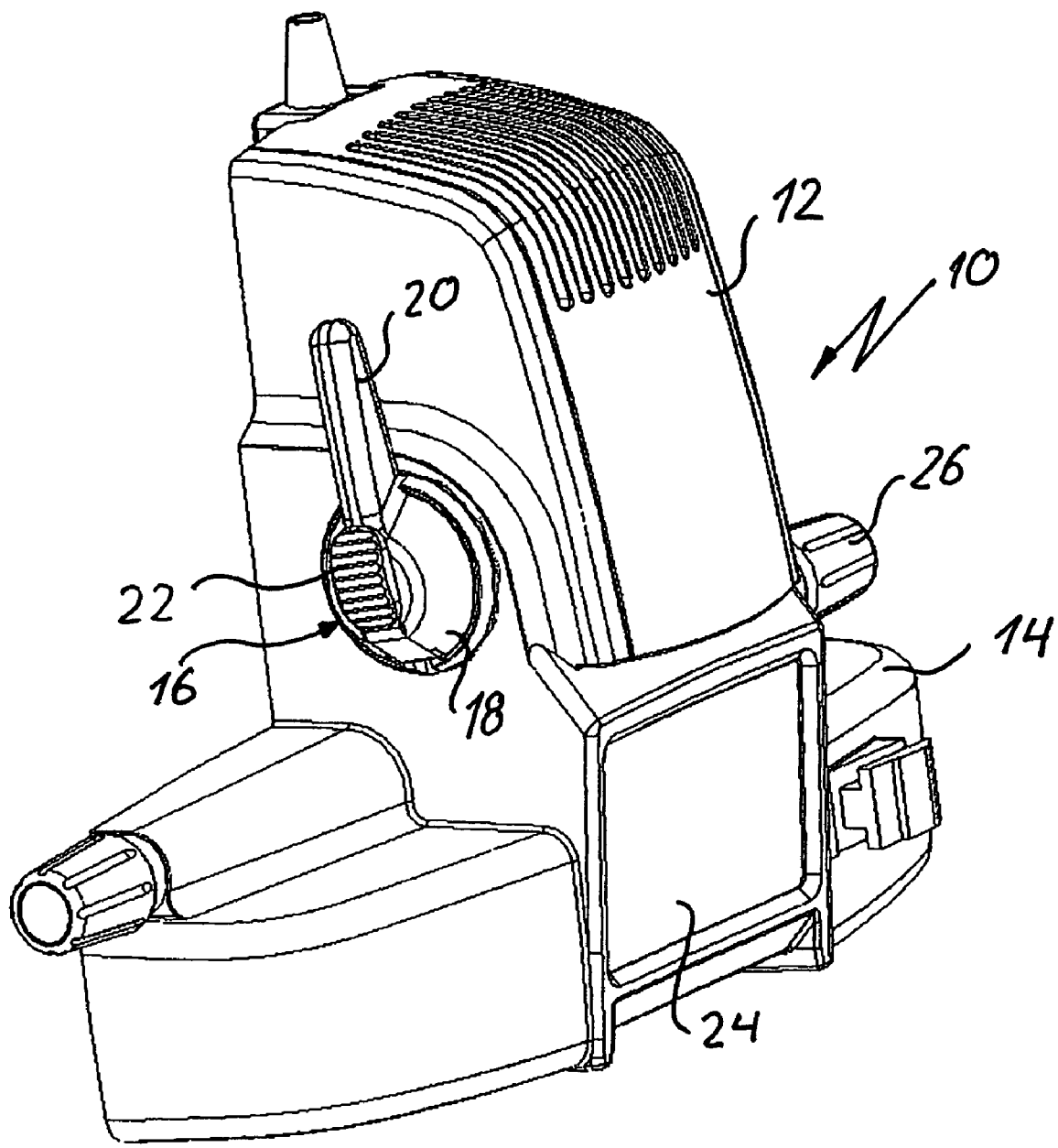

The invention relates to an ophthalmoscope having a housing in which there are arranged an observing unit and an illuminating unit between which there are/is arranged diaphragm means and/or filter means that can be set via a swivel lever means mounted outside on the housing.

2. Description of the Background Art

U.S. Pat. No. 4,684,227 discloses a generic binocular ophthalmoscope in whose lower housing part an observing unit is arranged by means of which an examiner can examine through a patient's pupil. An illuminating unit with a light source is accommodated in the upper housing part. An adjustable diaphragm is arranged between the light source and the observing unit. Also provided is a filter means by means of which optical filters can be moved into the illuminating path between the illuminating source and the observing unit. For the purpose of setting the diaphragm and the optical filters, there is respectively mounted on the side of the housing swivel lever means that comprises a rotary element, arranged in a bearing opening, on the outside of which a swivel lever is fastened. The swivel levers are kinematically connected to a mechanism for setting the diaphragm and/or the optical filters.

The swivel lever means are mounted in a freely rotatable fashion in the bearing openings. As a rule, ophthalmoscopes are used by a single investigator who prefers a specific setting of the diaphragms and/or the optical filters. Other settings are carried out only rarely. Since the swivel lever means are supported in a freely rotatable fashion, the diaphragm or the optical filters are, however, displaced when the swivel levers are lightly touched, and this quickly comes about during improper handling. It is then necessary to reset the diaphragm and filters.

SUMMARY OF THE INVENTION

It is the object of the invention to provide a reliable handheld ophthalmoscope with the aid of simple design means.

This object is achieved according to the invention by means of an ophthalmoscope comprising a housing in which an observing unit and a light source are arranged between which there is positioned at least one of diaphragm means and filter means that can be adjusted by swivel lever means mounted outside on said housing, wherein said swivel lever means can be locked in several locking positions by locking means.

In the case of the ophthalmoscope according to the invention, the respective swivel lever means can be locked in respective latch stages by locking means. This prevents the setting of the diaphragm and/or the filters from being changed when the swivel lever means is inadvertently touched. An investigator can lock the diaphragm and the filters in a position he desires.

It is advantageous for the locking means to be designed in such a way that it unlocks when a predetermined torque exerted on the swivel lever means is exceeded. This prevents the swivel lever means from being damaged when an excessive force is exerted on it.

In a preferred embodiment of the ophthalmoscope according to the invention, the swivel lever means comprises a rotary element that is rotatably supported in a bearing opening provided in the housing. A number of latching depressions are formed in the edge of the bearing opening at an angular distance from one another. In order to lock the rotary element in a desired position, a latching slide provided on the rotary element can optionally be brought into engagement with one of the latching depressions.

In this embodiment, the latching depressions and a tip of the latching slide have inclined sidewalls that bear against one another in the locking position of the latching slide. The inclination angle of the sidewalls in selected such that the latching slide moves out of the latching depression when a predetermined torque is applied to the rotary element, such that damage to the swivel lever means during application of an excessively large force is prevented.

DETAILED DESCRIPTION OF THE DRAWINGS

Figure 2:
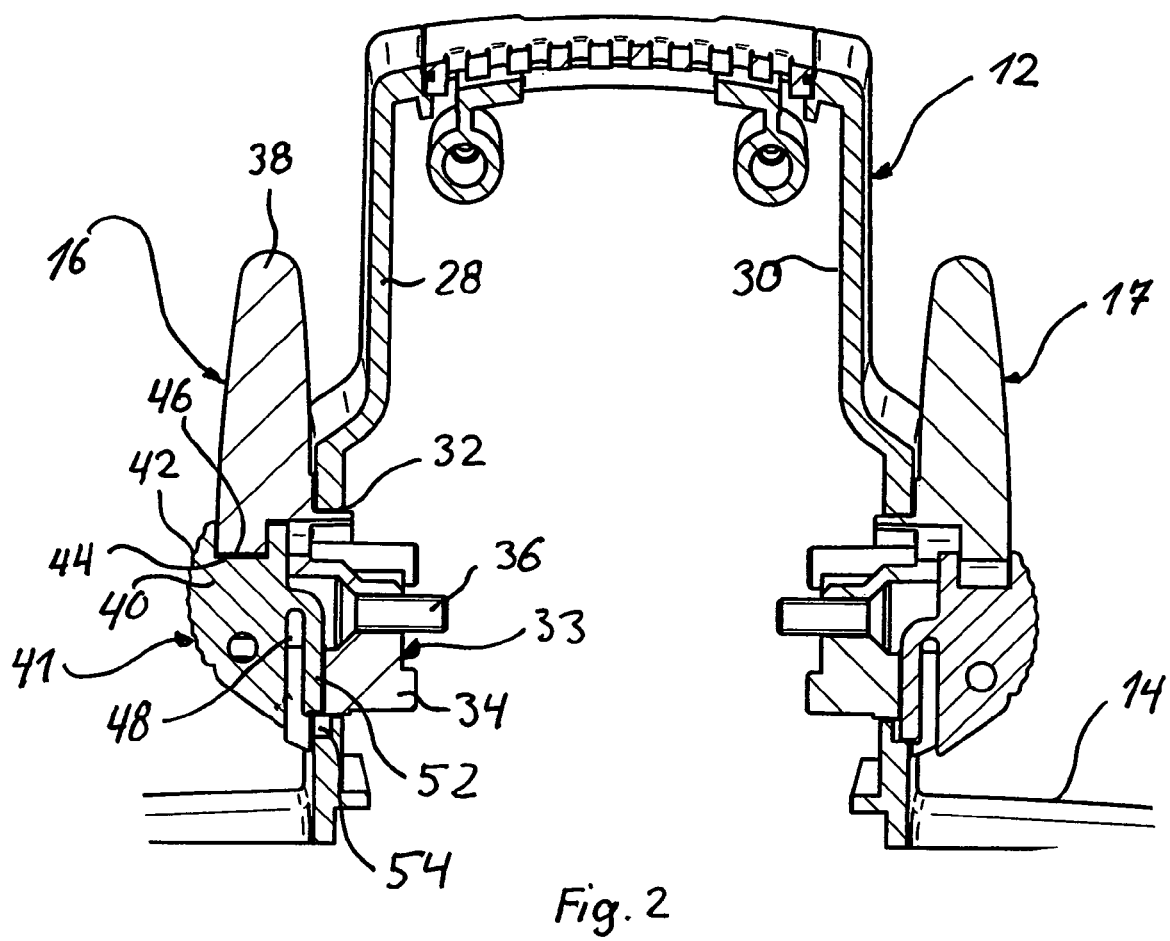
Figure 3:
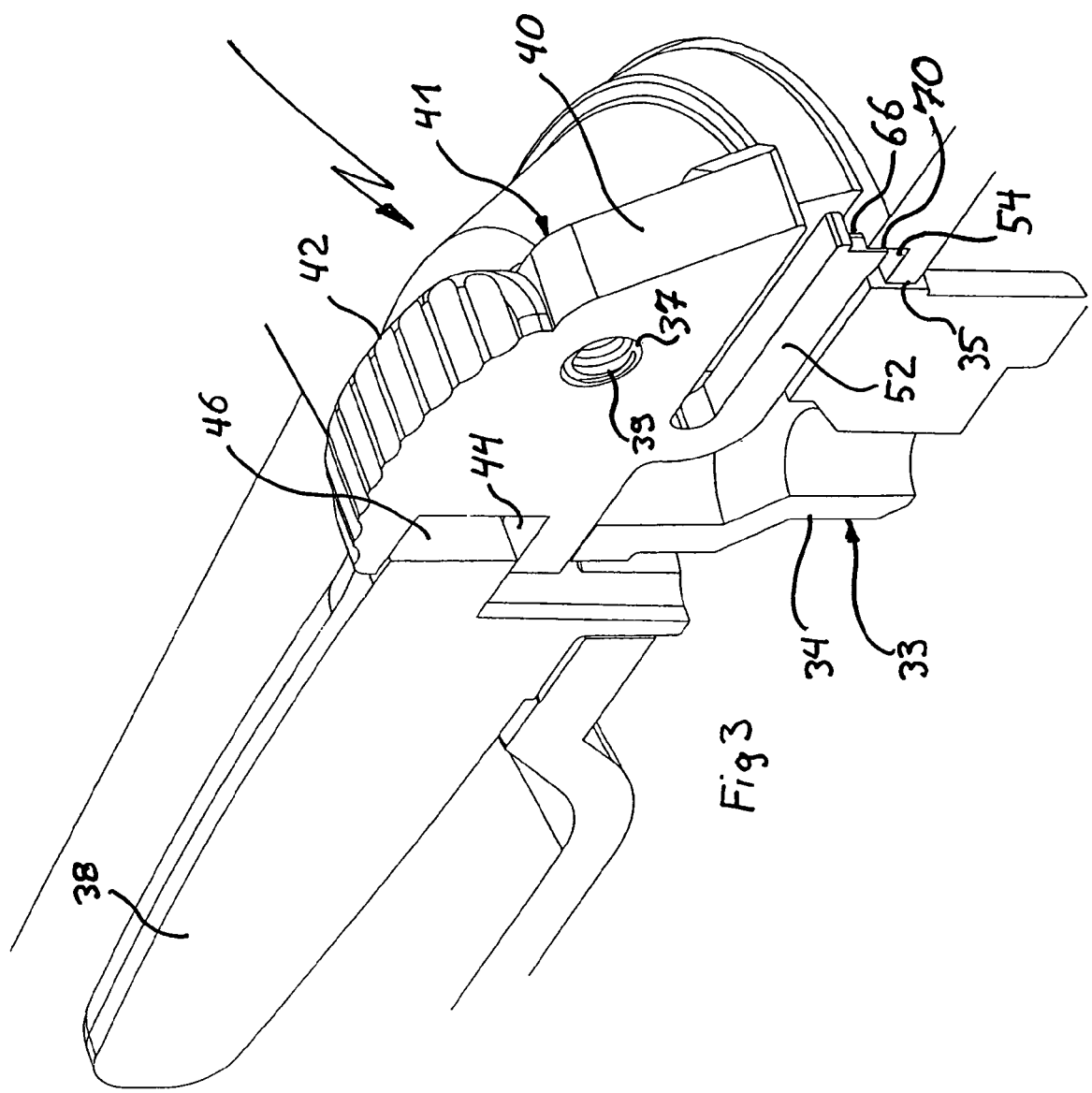
Figure 4:
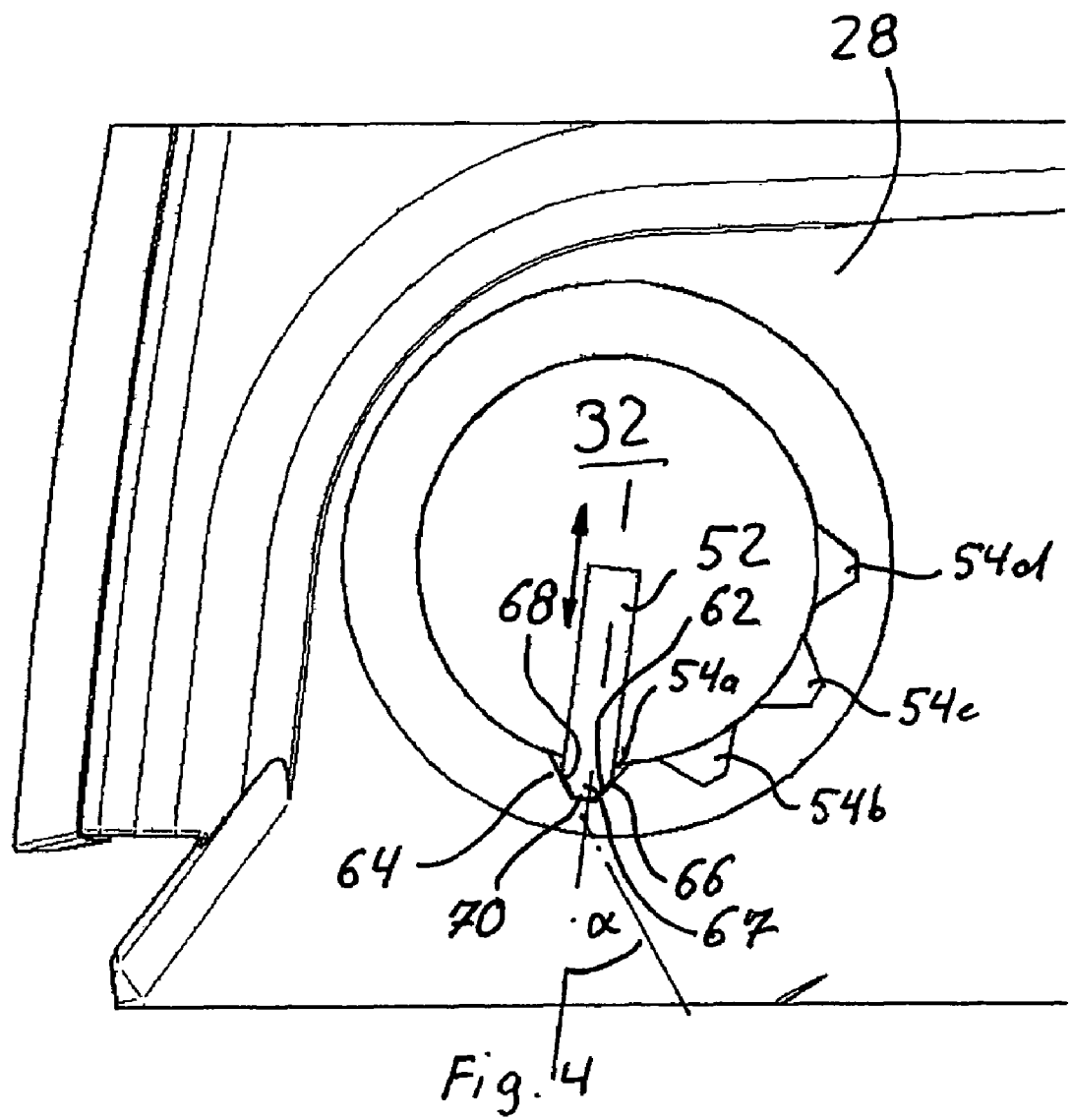
Figure 5:
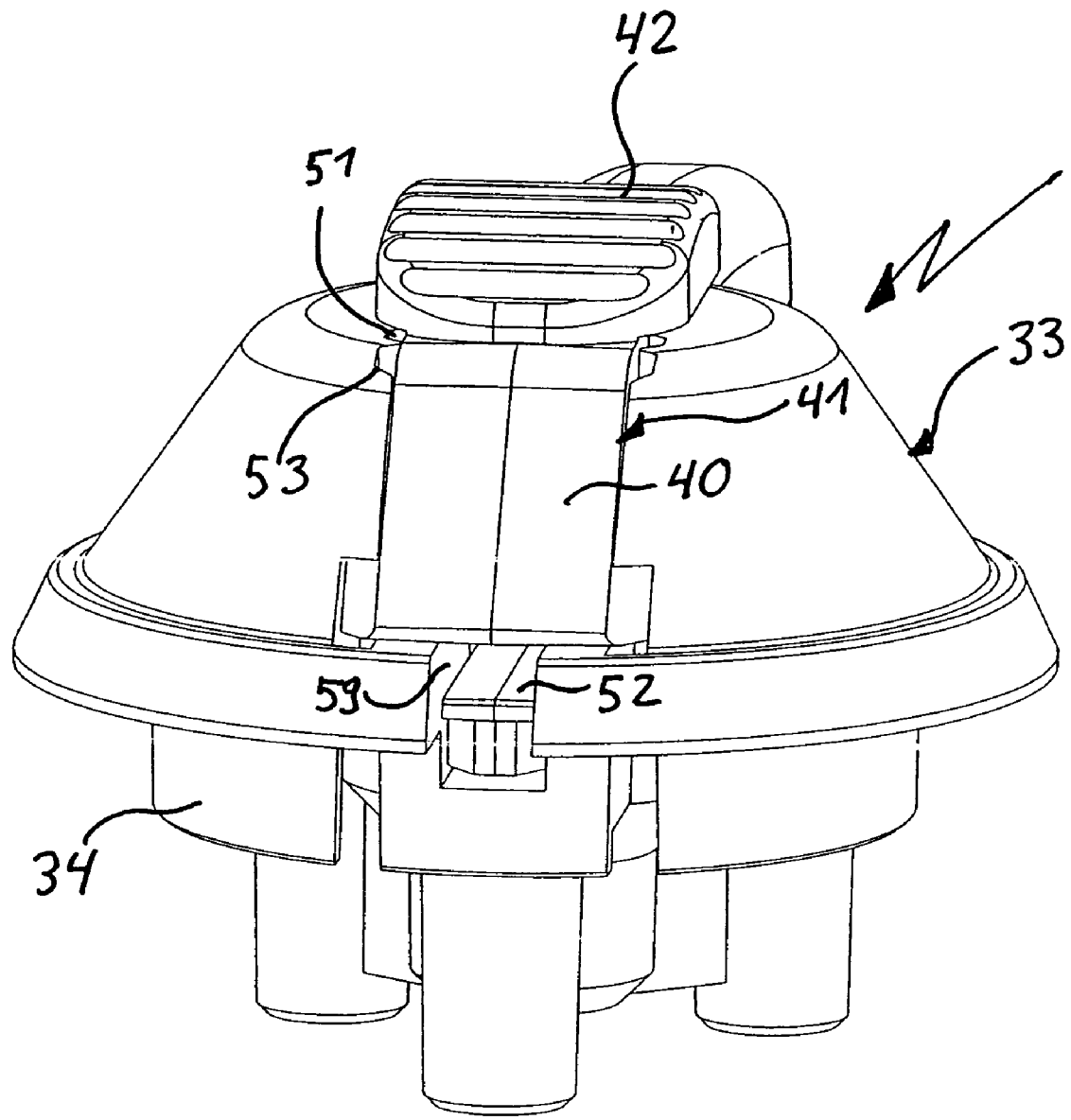

An exemplary embodiment of the invention is explained in more detail below with the aid of drawings, in which:

FIG. 1 shows an ophthalmoscope in a perspective fashion,

FIG. 2 shows a cross section through the upper part of the ophthalmoscope of FIG. 1, FIG. 3 shows a perspective longitudinal view of a swivel lever means of the ophthalmoscope of FIG. 1, FIG. 4 shows a schematic of the engagement of a latching slide of the locking means of FIG. 3 in latching depressions, FIG. 5 shows a perspective illustration of the swivel lever means of FIG. 3, and FIG. 6 shows a sectional side view of the swivel lever means of FIG. 3.

DETAILED DESCRIPTION OF THE INVENTION

As shown in FIG. 1, the ophthalmoscope 10 according to the invention comprises a lower housing part 14 in which an observing unit is arranged behind a central glass pane 42. The observing direction of the observing unit can be set by a setting rod 26.

Provided above the glass pane 24 is an upper housing part 12 in which an illuminating unit with an illuminating source, for example LEDs, is accommodated. Although it is not shown in the drawings for reasons of clarity, in the case of the ophthalmoscope according to the invention, as in the case of the opthalmoscope known from U.S. Pat. No. 4,684,227, there is firstly arranged between the light source and the observing unit an adjustable diaphragm means, after which there is arranged a filter means with optical filters in the illuminating path. The diaphragm means can be set by a swivel lever means 16 via a mechanism that is not shown. The setting of the filters is enabled by a swivel lever means 17 via a mechanism (likewise not shown).

Two swivel lever means 16, 17 are of identical design. For this reason, the construction of the swivel lever means 16, 17 is described with the aid of the swivel lever means 16 for the diaphragm means. A circular bearing opening 32 is provided in the corresponding sidewall 28 of the top housing part 12. An overall cylindrical bearing section 34 of a rotary element 33 is rotatably supported in the bearing opening 32. By means of a coaxial screw 36, the bearing section 34 is connected inside in a rotationally fixed fashion to the diaphragm means in order to adjust it.

Guided in the bearing section 34 such that it can be displaced in the radial direction of the bearing section 34 is a locking body 40 of a locking element 41 that extends beyond the outside of the bearing section 34 and has on its outside a fluted gripping surface 42.

Upwardly extending outside the upper housing part 12 from the bearing section 34 is a lever 38 that has in the region of the locking body 40 a downwardly extending shoulder 46 that, in the unlocking position, shown in FIG. 2, of the locking body 40, engages in a recess 44 on the top side of the locking body 40, and bears against the base thereof.

Extending radially downward approximately from the axis of rotation of the bearing section 34 at a distance from the vertically running inside of the locking body 40 is a narrow latching slide 52 designed integrally with the locking body 40. There is formed as a result between the locking body 40 and latching slide 52 a downwardly open U-shaped cutout 48 that extends radially downward and extends longitudinally. The latching slide 52 is guided radially at the side in a slot 59 in the bearing section 34.

As is to be seen in FIG. 4, there are formed in the edge 35 of the bearing opening 32 a number of latching depressions 54a, 54b, 54c, 54d that are open toward the axis of rotation and outwardly and have sidewalls 64, 66 that are inclined to the radial of the bearing opening 32 through the middle of the corresponding latching depression 54a, 54b, 54c, 54d at an angle $\alpha$, and are bounded by a tangentially running base 70. At its tip, the latching slide 52 has lateral surfaces 62, 68 that are inclined at the same angle as the lateral surfaces 64, 66 of the latching depressions 54a to 54d.

It is to be seen in FIG. 3 that a transversely running blind hole 37 in which a helical spring 39 is arranged is formed in the locking body 40. It is shown in FIG. 6, in which the locking body 40 is omitted for the purpose of clarity, that there is fastened at the end of the helical spring 39 a ball 43 which projects from the blind hole 37 in the unloaded state. Arranged at a distance from one another in the bearing section 34 in a fashion opposite the ball 43 are two substantially concave recesses 51, 53 in the displacement direction of the locking body 40, in which the ball 43 engages in the unlocking position or in the locking position of the locking body 40.

The ball 43 biased by the spring 39 ensures that the locking body 40 automatically latches in the unlocking position or in the locking position as soon as the ball 43 has overstepped the edge of the corresponding recess 51, 53.

If the diaphragm is to be fixed in a specific position, for the purpose of locking the swivel lever means 16 the locking body 40 is displaced downward in the radial direction until the tip of the latching slide 52 strikes the base of the corresponding latching depression 54a to 54d, and the sidewalls 62, 68 of the latching slide 52 bear against the sidewalls 64, 66 of the corresponding depressions 54a to 54d. The swivel lever means 16 is thereby locked. As a result, an inadvertent misadjustment of the swivel lever means 16, and thus of the diaphragm is prevented. The inclination of the lateral surfaces 62, 64, 66, 68, and the resistance of the locking body 40 in the radial direction are, however, selected such that in the event of a force that exceeds a previously determined force, the latching slide 52 is moved out of the corresponding latching depression 54a or 54d. This prevents damage to the swivel lever means 16. The inclination angle $\alpha$ is a function of the coefficient of friction between the lateral surfaces 62, 64, 66, 68 and the force that is required in order to move the locking body 40 in the unlocking direction. The angle $\alpha$ is preferably between 10 and 80 degrees.

As the swivel lever means 17 is designed like the swivel lever means 16, the filters can be fixed in the same way as described above.

The invention claimed is:

1. An ophthalmoscope comprising a housing in which an observing unit and a light source are arranged between which there is positioned at least one of diaphragm means and filter means that can be adjusted by swivel lever means mounted outside on said housing, wherein said swivel lever means can be locked in several locking positions by locking means, wherein said swivel lever means comprises a rotary element that is rotatably supported in a bearing opening provided in said housing, wherein a number of latching depressions are formed in an edge of said bearing opening at an angular distance from one another, and wherein there is provided on said rotary element a latching slide that can optionally be brought into engagement with one of the latching depressions in order to lock said rotary element in a desired position.

2. An ophthalmoscope as claimed in claim 1, wherein said latching depressions and a tip of said latching slide have inclined sidewalls that bear against one another in said locking position of said latching slide, an inclination angle of said sidewalls being selected such that said latching slide moves out of said latching depression when a predetermined torque Is applied to said rotary element.

3. An ophthalmoscope comprising a housing in which an observing unit and a light source are arranged between which there is positioned at least one of diaphragm means and filter means that can be adjusted by swivel lever means mounted outside on said housing, wherein said swivel lever means can be locked in several locking positions by locking means, wherein said locking means is designed in such a way that it unlocks when a predetermined torque exerted on said swivel lever means is exceeded, said swivel lever means comprises a rotary element that is rotatably supported in a bearing opening provided in said housing, a number of latching depressions being formed in an edge of said bearing opening at an angular distance from one another, and a latching slide being provided on said rotary element that can optionally be brought into engagement with one of the latching depressions in order to lock said rotary element in a desired position, and said latching depressions and a tip of said latching slide have inclined sidewalls that bear against one another in said locking position of said latching side, an inclination angle of said sidewalls being selected such that said latching slide moves out of said latching depression when a predetermined torque is applied to said rotary element.

\* \* \* \* \*